(12) United States Patent
Uspenski et al.

(10) Patent No.: US 11,596,434 B2
(45) Date of Patent: Mar. 7, 2023

(54) ENDOSCOPIC SNARE DEVICE

(71) Applicant: UNITED STATES ENDOSCOPY GROUP, INC., Mentor, OH (US)

(72) Inventors: Alex Uspenski, Chardon, OH (US); Christopher J. Kaye, Berea, OH (US); Reza Mohammadpour, Willoughby Hills, OH (US); Craig Moore, Pepper Pike, OH (US); Cynthia Ann Ranallo, Eastlake, OH (US); John Winstanley, Madison, OH (US)

(73) Assignee: UNITED STATES ENDOSCOPY GROUP, INC., Mentor, OH (US)

( * ) Notice: Subject to any disclaimer, the term of this patent is extended or adjusted under 35 U.S.C. 154(b) by 404 days.

(21) Appl. No.: 16/847,274

(22) Filed: Apr. 13, 2020

(65) Prior Publication Data

US 2020/0237396 A1   Jul. 30, 2020

Related U.S. Application Data

(63) Continuation of application No. 15/866,401, filed on Jan. 9, 2018, now Pat. No. 10,667,838.
(Continued)

(51) Int. Cl.
*A61B 17/3205* (2006.01)
*A61B 17/00* (2006.01)
(Continued)

(52) U.S. Cl.
CPC .. *A61B 17/32056* (2013.01); *A61B 17/00234* (2013.01); *A61B 17/221* (2013.01);
(Continued)

(58) Field of Classification Search
CPC ........ A61B 17/32056; A61B 17/00234; A61B 17/221; A61B 17/320016; A61B 90/92;
(Continued)

(56) References Cited

U.S. PATENT DOCUMENTS 2,197,921 A   4/1940   Brown
2,626,447 A   4/1940   Hunt
(Continued)

FOREIGN PATENT DOCUMENTS

DE   19938902 A1   4/2000
EP    0446020 A1   9/1991
(Continued)

OTHER PUBLICATIONS

Extended Search Report from European Application No. 20181554.5 dated Oct. 2, 2020.
(Continued)

*Primary Examiner* — Phong Son H Dang
(74) *Attorney, Agent, or Firm* — Calfee, Halter & Griswold LLP

(57) ABSTRACT

The present subject matter discloses a tissue removal tool for use with an endoscope. The tool comprises a loop formed by a piece of wire and movable between an open position and a closed position, and a transmitting assembly comprising: a handle; and a link having a first end attached to the handle and a second end attached to the loop, the loop portion being movable between the open and closed position by action of the handle. The loop is defined in the open position by a proximal portion and a distal portion. The widest portion of the loop is more proximal to a proximal end of the loop than the mid-point of the length of the loop is.

39 Claims, 8 Drawing Sheets

Related U.S. Application Data

(60) Provisional application No. 62/444,144, filed on Jan. 9, 2017.

(51) Int. Cl.
*A61B 90/92* (2016.01)
*A61B 17/221* (2006.01)
*A61B 17/32* (2006.01)

(52) U.S. Cl.
CPC ...... *A61B 17/320016* (2013.01); *A61B 90/92* (2016.02); *A61B 2017/00358* (2013.01); *A61B 2017/00367* (2013.01); *A61B 2017/00438* (2013.01); *A61B 2017/2212* (2013.01); *A61B 2017/2217* (2013.01)

(58) Field of Classification Search
CPC .......... A61B 2017/00358; A61B 2019/00367; A61B 2017/2212; A61B 2017/2217
See application file for complete search history.

(56) References Cited

U.S. PATENT DOCUMENTS

| | | |
|---|---|---|
| 3,805,791 A | 4/1974 | Seuberth et al. |
| 4,083,706 A | 4/1978 | Wiley |
| 4,146,019 A | 3/1979 | Bass et al. |
| 4,200,104 A | 4/1980 | Harris |
| 4,202,338 A | 5/1980 | Bitrolf |
| 4,256,113 A | 3/1981 | Chamness |
| 4,311,143 A | 1/1982 | Komlya |
| 4,493,320 A | 1/1985 | Treat |
| 4,905,691 A | 3/1990 | Rydell |
| 4,966,589 A | 10/1990 | Kaufman |
| 5,009,642 A | 4/1991 | Sahi |
| 5,057,114 A | 10/1991 | Wittich et al. |
| 5,059,199 A | 10/1991 | Okada et al. |
| 5,078,716 A * | 1/1992 | Doll ...................... A61B 18/14 606/47 |
| 5,084,054 A | 1/1992 | Bencini et al. |
| 5,098,441 A | 3/1992 | Wechler |
| 5,122,147 A * | 6/1992 | Sewell, Jr. ....... A61B 17/32056 606/116 |
| 5,123,906 A | 6/1992 | Kelman |
| 5,147,371 A | 9/1992 | Washington |
| 5,156,590 A | 10/1992 | Vilmar |
| 5,171,233 A | 12/1992 | Amplatz et al. |
| 5,190,542 A | 3/1993 | Nakao |
| 5,192,280 A | 3/1993 | Parins |
| 5,192,286 A | 3/1993 | Phan et al. |
| 5,201,740 A | 4/1993 | Nakao et al. |
| 5,207,686 A * | 5/1993 | Dolgin ............. A61B 17/32056 606/49 |
| 5,279,548 A | 1/1994 | Essig et al. |
| 5,281,238 A | 1/1994 | Chin |
| 5,336,227 A | 8/1994 | Nakao et al. |
| 5,354,303 A | 10/1994 | Spaeth et al. |
| 5,373,854 A | 12/1994 | Kolozsi |
| 5,374,273 A | 12/1994 | Nakao et al. |
| 5,376,094 A | 12/1994 | Kline |
| 5,417,697 A | 5/1995 | Wilk et al. |
| 5,423,830 A | 6/1995 | Schneebaum et al. |
| 5,441,503 A | 8/1995 | Considine et al. |
| 5,449,372 A | 9/1995 | Schmaitz et al. |
| 5,480,404 A | 1/1996 | Kammerer et al. |
| 5,496,330 A | 3/1996 | Bates et al. |
| 5,501,692 A | 3/1996 | Riza |
| 5,536,248 A | 7/1996 | Weaver et al. |
| 5,542,948 A | 8/1996 | Weaver et al. |
| 5,599,299 A | 2/1997 | Weaver et al. |
| 5,599,300 A | 2/1997 | Weaver et al. |
| 5,643,283 A | 7/1997 | Younker |
| 5,666,970 A | 9/1997 | Smith |
| 5,741,271 A | 4/1998 | Nakao et al. |
| 5,759,187 A * | 6/1998 | Nakao .................... A61B 1/018 606/113 |
| 5,779,686 A | 7/1998 | Sato et al. |
| 5,782,840 A * | 7/1998 | Nakao .................... A61B 18/14 606/113 |
| 5,785,689 A | 7/1998 | de Toledo |
| 5,788,681 A | 8/1998 | Weaver et al. |
| 5,810,776 A | 9/1998 | Bacich et al. |
| 5,843,028 A | 12/1998 | Weaver et al. |
| 5,843,051 A | 12/1998 | Adams et al. |
| 5,846,248 A | 12/1998 | Chu et al. |
| 5,860,987 A | 1/1999 | Ratcliff et al. |
| 5,906,594 A | 5/1999 | Scarfone et al. |
| 5,906,621 A | 5/1999 | Secrest et al. |
| 5,947,979 A | 9/1999 | Ouchi et al. |
| 5,961,526 A | 10/1999 | Chu et al. |
| 5,964,740 A | 10/1999 | Ouchi et al. |
| 5,971,994 A | 10/1999 | Fritzsch |
| 5,971,995 A | 10/1999 | Rousseau |
| 5,976,073 A | 11/1999 | Ouchi |
| 5,989,264 A | 11/1999 | Wright |
| 5,997,547 A | 12/1999 | Nakao et al. |
| 6,007,546 A | 12/1999 | Snow et al. |
| 6,010,512 A | 1/2000 | Chu et al. |
| 6,015,391 A | 1/2000 | Rishton et al. |
| 6,015,415 A | 1/2000 | Avellanet |
| 6,050,995 A | 4/2000 | Durgin |
| 6,068,603 A | 5/2000 | Suzuki |
| 6,093,195 A * | 7/2000 | Ouchi .................... A61B 18/14 606/113 |
| 6,123,665 A * | 9/2000 | Kawano ............. A61B 17/3478 606/113 |
| 6,142,956 A | 11/2000 | Kortenbach et al. |
| 6,171,315 B1 | 1/2001 | Chu et al. |
| 6,174,291 B1 | 1/2001 | McMahon et al. |
| 6,183,482 B1 | 2/2001 | Bates et al. |
| 6,190,353 B1 | 2/2001 | Makower et al. |
| 6,193,672 B1 | 2/2001 | Clement |
| 6,210,416 B1 | 4/2001 | Chu et al. |
| 6,235,026 B1 * | 5/2001 | Smith ............... A61B 17/32056 606/113 |
| 6,245,078 B1 * | 6/2001 | Ouchi ............... A61B 17/32056 606/113 |
| 6,264,664 B1 * | 7/2001 | Avellanet .......... A61B 17/221 606/1 |
| 6,299,612 B1 | 10/2001 | Ouchi |
| 6,315,782 B1 | 11/2001 | Chu et al. |
| 6,319,260 B1 | 11/2001 | Yamamoto |
| 6,352,503 B1 | 3/2002 | Matsui et al. |
| 6,375,661 B2 | 4/2002 | Chu et al. |
| 6,383,194 B1 | 5/2002 | Pothula |
| 6,383,198 B1 | 5/2002 | Hamilton |
| 6,407,333 B1 | 6/2002 | Schroen |
| 6,409,733 B1 | 6/2002 | Conlon et al. |
| 6,440,138 B1 | 8/2002 | Reiley et al. |
| 6,458,074 B1 | 10/2002 | Matsui et al. |
| 6,500,182 B2 | 12/2002 | Foster |
| 6,527,753 B2 | 3/2003 | Sekine et al. |
| 6,527,781 B2 | 3/2003 | Bates et al. |
| 6,602,262 B2 | 8/2003 | Griego et al. |
| 6,616,654 B2 | 9/2003 | McIennauer |
| 6,616,659 B1 | 9/2003 | de la Torre et al. |
| 6,669,716 B1 | 12/2003 | Gilson et al. |
| 6,730,097 B2 | 5/2004 | Dennis |
| 6,743,228 B2 | 6/2004 | Lee et al. |
| 6,770,066 B1 | 8/2004 | Weaver et al. |
| 6,773,432 B1 | 8/2004 | Clayman et al. |
| 6,827,710 B1 | 12/2004 | Money et al. |
| 6,945,956 B2 | 9/2005 | Waldhauser et al. |
| 6,960,172 B2 | 11/2005 | McGuckin, Jr. |
| 7,001,354 B2 | 2/2006 | Suzuki et al. |
| 7,037,291 B2 | 5/2006 | Lee et al. |
| 7,037,307 B2 | 5/2006 | Dennis |
| 7,041,116 B2 | 5/2006 | Goto et al. |
| 7,044,947 B2 | 5/2006 | de la Torre et al. |
| 7,104,990 B2 | 9/2006 | Jenkins et al. |
| 7,122,003 B2 | 10/2006 | Nakao |
| 7,147,635 B2 | 12/2006 | Ciarrocca |
| 7,270,663 B2 | 9/2007 | Nakao |

(56) References Cited

U.S. PATENT DOCUMENTS

| | | | |
|---|---|---|---|
| 7,387,632 B2 | 6/2008 | Ouchi | |
| 7,547,310 B2 | 6/2009 | Whitfield | |
| 7,575,585 B2 | 8/2009 | Goto et al. | |
| 7,632,294 B2 | 12/2009 | Milbodker et al. | |
| 7,691,110 B2 | 4/2010 | Secrest et al. | |
| 7,704,249 B2 | 4/2010 | Woloszko et al. | |
| 7,758,591 B2 | 7/2010 | Griego et al. | |
| 7,785,250 B2 | 8/2010 | Nakao | |
| 7,951,073 B2 | 5/2011 | Freed | |
| 7,972,265 B1 | 7/2011 | Chin et al. | |
| 8,016,838 B2 * | 9/2011 | Kaye | A61B 17/221 606/113 |
| 8,066,689 B2 | 11/2011 | Mitelberg et al. | |
| 8,070,756 B2 | 12/2011 | Secrest | |
| 8,075,572 B2 | 12/2011 | Stefanchik et al. | |
| 8,100,905 B2 | 1/2012 | Weitzner | |
| 8,114,099 B2 | 2/2012 | Shipp | |
| 8,128,592 B2 | 3/2012 | Mitelberg et al. | |
| 8,167,893 B2 | 5/2012 | Motosugi | |
| 8,187,266 B2 | 5/2012 | Dickens et al. | |
| 8,216,272 B2 | 7/2012 | Shipp | |
| 8,241,210 B2 | 8/2012 | Lunsford et al. | |
| 8,267,933 B2 | 9/2012 | Hamou | |
| 8,282,658 B2 | 10/2012 | Knapp et al. | |
| 8,298,243 B2 | 10/2012 | Carlton et al. | |
| 8,317,771 B2 | 11/2012 | Mitelberg et al. | |
| 8,328,803 B2 | 12/2012 | Regadas | |
| 8,343,168 B2 | 1/2013 | Kaye et al. | |
| 8,357,148 B2 | 1/2013 | Boulais et al. | |
| 8,366,612 B2 | 2/2013 | Rosenthal | |
| 8,372,066 B2 | 2/2013 | Manwaring et al. | |
| 8,388,630 B2 | 3/2013 | Teague et al. | |
| 8,591,521 B2 | 11/2013 | Cherry et al. | |
| 9,572,591 B2 | 2/2017 | Haack | |
| 9,872,700 B2 | 1/2018 | Haack | |
| 10,285,725 B2 | 5/2019 | Fleury | |
| 11,382,987 B2 | 7/2022 | Callan | |
| 2002/0049423 A1 | 4/2002 | Howell et al. | |
| 2002/0091394 A1 * | 7/2002 | Reynolds | A61B 17/00234 606/127 |
| 2002/0107569 A1 | 8/2002 | Katsura | |
| 2002/0151889 A1 | 10/2002 | Swanson et al. | |
| 2003/0004538 A1 * | 1/2003 | Secrest | A61B 17/221 606/200 |
| 2003/0139750 A1 * | 7/2003 | Shinozuka | A61B 17/32056 606/113 |
| 2003/0195470 A1 | 10/2003 | Ponzi | |
| 2003/0195492 A1 | 10/2003 | Gobron et al. | |
| 2003/0216753 A1 | 11/2003 | Nishtala et al. | |
| 2003/0236519 A1 | 12/2003 | Kear | |
| 2004/0059352 A1 | 3/2004 | Burbank et al. | |
| 2004/0092953 A1 * | 5/2004 | Salameh | A61B 18/14 606/113 |
| 2004/0158127 A1 | 8/2004 | Okada | |
| 2005/0085808 A1 | 4/2005 | Nakao | |
| 2005/0107668 A1 | 5/2005 | Smith | |
| 2005/0267489 A1 * | 12/2005 | Secrest | A61B 17/22 606/113 |
| 2005/0267490 A1 | 12/2005 | Secrest et al. | |
| 2006/0009759 A1 | 1/2006 | Christian et al. | |
| 2006/0058776 A1 | 3/2006 | Bilsbury | |
| 2006/0229640 A1 * | 10/2006 | Whitfield | A61B 17/221 606/114 |
| 2006/0235433 A1 | 10/2006 | Secrest | |
| 2006/0264977 A1 | 11/2006 | Dana et al. | |
| 2007/0016225 A1 * | 1/2007 | Nakao | A61B 17/221 606/114 |
| 2007/0250070 A1 | 10/2007 | Nobis et al. | |
| 2007/0288035 A1 | 12/2007 | Okada | |
| 2008/0045945 A1 | 2/2008 | Hamou | |
| 2008/0183184 A1 | 7/2008 | Kaye et al. | |
| 2008/0306336 A1 | 12/2008 | Kaye | |
| 2009/0043317 A1 | 2/2009 | Cavanaugh et al. | |
| 2009/0112244 A1 | 4/2009 | Freudenthal | |
| 2010/0036375 A1 * | 2/2010 | Regadas | A61B 17/32056 606/113 |
| 2010/0069925 A1 | 3/2010 | Friedman | |
| 2010/0268206 A1 | 10/2010 | Manwaring et al. | |
| 2010/0268216 A1 | 10/2010 | Manwaring | |
| 2011/0106077 A1 | 5/2011 | Yanuma et al. | |
| 2011/0106107 A1 | 5/2011 | Binmoeller et al. | |
| 2012/0004666 A1 | 1/2012 | Cowley et al. | |
| 2012/0046667 A1 * | 2/2012 | Cherry | A61B 17/221 606/113 |
| 2012/0172662 A1 * | 7/2012 | Kappel | A61B 17/32056 606/113 |
| 2012/0172864 A1 * | 7/2012 | Farin | A61B 18/14 606/33 |
| 2012/0184967 A1 | 7/2012 | Saleh | |
| 2012/0283723 A1 * | 11/2012 | Jenkins | A61B 18/14 606/41 |
| 2013/0018384 A1 | 1/2013 | Kappel et al. | |
| 2013/0018385 A1 * | 1/2013 | Keene | A61B 17/32056 606/113 |
| 2014/0276810 A1 * | 9/2014 | Raybin | A61B 17/32056 606/46 |
| 2014/0276911 A1 * | 9/2014 | Smith | A61B 17/32056 606/113 |
| 2015/0025555 A1 | 1/2015 | Sos | |
| 2015/0066045 A1 * | 3/2015 | Haack | A61B 17/32056 606/113 |
| 2015/0105789 A1 * | 4/2015 | Raybin | A61B 17/32056 606/113 |
| 2015/0157345 A1 * | 6/2015 | Haack | A61B 17/32056 606/113 |
| 2016/0242804 A1 * | 8/2016 | Fleury | A61B 17/32056 |
| 2016/0279393 A1 | 9/2016 | Anderson | |
| 2017/0007277 A1 * | 1/2017 | Drapeau | A61B 17/320016 |
| 2017/0049471 A1 * | 2/2017 | Gaffney | A61B 17/32056 |
| 2017/0231647 A1 * | 8/2017 | Saunders | A61B 17/221 606/113 |
| 2018/0028220 A1 * | 2/2018 | Smith | A61B 18/1485 |
| 2018/0049766 A1 * | 2/2018 | Nolan | A61B 17/32056 |
| 2018/0049873 A1 | 2/2018 | Manash | |

FOREIGN PATENT DOCUMENTS

| | | |
|---|---|---|
| EP | 463363 A2 | 1/1992 |
| EP | 758551 A1 | 2/1997 |
| EP | 1180349 A1 | 2/2002 |
| EP | 1870015 A1 | 12/2007 |
| JP | S 57-078843 A | 5/1982 |
| JP | S 63-197442 A | 8/1988 |
| JP | 3-54652 | 5/1991 |
| JP | 5-091686 | 4/1993 |
| JP | 3250621 | 8/1993 |
| JP | H10234743 A | 4/1995 |
| JP | 10-071166 | 3/1998 |
| JP | 10-174688 | 6/1998 |
| JP | 11-047154 | 2/1999 |
| JP | 11-226024 | 8/1999 |
| JP | 2000-175930 | 6/2000 |
| JP | 2000-210295 | 8/2000 |
| JP | 2000-316868 | 11/2000 |
| JP | 2000-342600 | 12/2000 |
| JP | 2003-052707 | 2/2003 |
| JP | 2003-511140 | 3/2003 |
| JP | 2006-087473 A | 4/2006 |
| JP | 2007-534451 | 11/2007 |
| JP | 2010-528785 A | 8/2010 |
| JP | 2011-526188 A | 10/2011 |
| JP | 2015-163238 A | 9/2015 |
| JP | 2016-087151 A | 5/2016 |
| JP | 2016-530965 A | 12/2018 |
| WO | 93/015671 A1 | 8/1993 |
| WO | 99/42041 A1 | 8/1999 |
| WO | 99/51159 A1 | 10/1999 |
| WO | 02/094082 A2 | 11/2002 |
| WO | 03/105674 A2 | 12/2003 |
| WO | 05/115116 A2 | 12/2005 |
| WO | 2006112231 A1 | 10/2006 |
| WO | 2007000452 A2 | 1/2007 |

(56) References Cited

FOREIGN PATENT DOCUMENTS

| WO | 2008044615 A1 | 4/2008 |
|---|---|---|
| WO | 08/094931 A2 | 8/2008 |
| WO | 08/154406 A1 | 12/2008 |
| WO | 2016044729 | 3/2016 |
| WO | 2016126974 | 8/2016 |

OTHER PUBLICATIONS

Search Report from European Application No. 18736653.9 dated Oct. 12, 2020.
International Search Report and Written Opinion from PCT/US02/15465 dated Aug. 26, 2003.
International Preliminary Examination Report from PCT/US02/15465 dated Nov. 12, 2003.
International Search Report from and Written Opinion from PCT/US05/18294 dated Jul. 3, 2007, 6 pgs.
International Search Report and Written Opinion from PCT/US05/18497 dated May 8, 2008.
International Search Report and Written Opinion from PCT/US08/52342 dated Jul. 30, 2008.
International Search Report and Written Opinion from PCT/US08/066161 dated Sep. 22, 2008.
International Search Report and Written Opinion from PCT/US2014/053828 dated Dec. 30, 2014.
International Preliminary Report on Patentability from PCT/US2014/053828 dated Mar. 8, 2016.
International Search Report and Written Opinion from PCT/US18/13017 dated Apr. 6, 2018.
Office Action from U.S. Appl. No. 11/137,814 dated May 16, 2007.
Response from U.S. Appl. No. 11/137,814 dated Aug. 16, 2007.
Office Action from U.S. Appl. No. 11/137,814 dated Dec. 7, 200.
Response from U.S. Appl. No. 11/137,814 dated Apr. 7, 2008.
Office Action from U.S. Appl. No. 11/137,814 dated Jul. 18, 2008.
Response from U.S. Appl. No. 11/137,814 dated Sep. 18, 2008.
Interview Summary and Advisory Action from U.S. Appl. No. 11/137,814 dated Oct. 14, 2008.
Response from U.S. Appl. No. 11/137,814 dated Nov. 18, 2008.
Office Action from U.S. Appl. No. 11/137,814 dated Feb. 12, 2009.
Response from U.S. Appl. No. 11/137,814 dated Aug. 12, 2009.
Office Action from U.S. Appl. No. 11/137,814 dated Nov. 23, 2009.
Response from U.S. Appl. No. 11/137,814 dated Jan. 19, 2010.
Notice of Allowance from U.S. Appl. No. 11/137,814 dated Feb. 18, 2010.
Office Action from U.S. Appl. No. 11/404,345 dated Jun. 27, 2008.
Interview Summary from U.S. Appl. No. 11/404,345 dated Oct. 7, 2008.
Response from U.S. Appl. No. 11/404,345 dated Nov. 26, 2008.
Office Action from U.S. Appl. No. 11/404,345 dated Mar. 11, 2010.
Response from U.S. Appl. No. 11/404,345 dated May 11, 2010.
Advisory Action from U.S. Appl. No. 11/404,345 dated May 27, 2010.
Response from U.S. Appl. No. 11/404,345 dated Sep. 13, 2010.
Office Action from U.S. Appl. No. 11/404,345 dated Dec. 29, 2010.
Response from U.S. Appl. No. 11/404,345 dated May 25, 2011.
Notice of Allowance from U.S. Appl. No. 11/404,345 dated Aug. 19, 2011.
Office Action from U.S. Appl. No. 12/021,903 dated Dec. 10, 2009.
Response from U.S. Appl. No. 12/021,903 dated Jun. 9, 2010.
Office Action from U.S. Appl. No. 12/021,903 dated Aug. 5, 2010.
Response from U.S. Appl. No. 12/021,903 dated Oct. 7, 2010.
Interview Summary from U.S. Appl. No. 12/021,903 dated Oct. 15, 2010.
Office Action from U.S. Appl. No. 12/021,903 dated Dec. 29, 2011.
Interview Summary from U.S. Appl. No. 12/021,903 date Mar. 21, 2012.
Response from U.S. Appl. No. 12/021,903 dated May 25, 2012.
Notice of Allowance from U.S. Appl. No. 12/021,903 dated Aug. 9, 2012.
Notice of Allowance from U.S. Appl. No. 12/021,903 dated Nov. 20, 2012.
Office Action from U.S. Appl. No. 14/016,906 dated Apr. 8, 2015.
Response to Office Action from U.S. Appl. No. 14/016,906 dated Feb. 12, 2016.
Office Action from U.S. Appl. No. 14/016,906 dated May 31, 2016.
Response to Office Action from U.S. Appl. No. 14/016,906 dated Jul. 28, 2016.
Office Action from U.S. Appl. No. 14/016,906 dated Sep. 13, 2016.
Response to Office Action from U.S. Appl. No. 14/016,906 dated Dec. 13, 2016.
Office Action from U.S. Appl. No. 14/016,906 dated Mar. 10, 2017.
Response to Office Action from U.S. Appl. No. 14/016,906 dated Aug. 10, 2017.
Office Action from U.S. Appl. No. 16/856,550 dated Nov. 10, 2021.
Notice of Allowance from U.S. Appl. No. 14/016,906 dated Sep. 27, 2017.
Office Action from U.S. Appl. No. 14/565,024 dated Apr. 17, 2015.
Response to Office Action from U.S. Appl. No. 14/565,024 dated Aug. 17, 2015.
Response to Office Action from U.S. Appl. No. 14/565,024 dated Mar. 25, 2016.
Advisory Action from U.S. Appl. No. 14/565,024 dated Apr. 14, 2016.
Office Action from U.S. Appl. No. 14/565,024 dated Jul. 5, 2016.
Amendment from U.S. Appl. No. 14/565,024 dated Jul. 28, 2016.
Notice of Allowance from U.S. Appl. No. 14/565,024 dated Aug. 30, 2016.
Office Action from U.S. Appl. No. 15/401,545 dated Aug. 2, 2018.
Response to Office Action from U.S. Appl. No. 15/401,545 dated Oct. 30, 2018.
Office Action from U.S. Appl. No. 15/401,545 dated Mar. 8, 2019.
Response to Office Action Office Action from U.S. Appl. No. 15/401,545 dated Jun. 10, 2019.
Office Action from U.S. Appl. No. 15/401,545 dated Jun. 27, 2019.
Response to Office Action Office Action from U.S. Appl. No. 15/401,545 dated Sep. 26, 2019.
Notice of Allowance from U.S. Appl. No. 15/401,545 dated Jan. 16, 2020.
Notice of Allowance from U.S. Appl. No. 15/866,401 dated Jan. 23, 2020.
Notice of Allowance from U.S. Appl. No. 15/866,401 dated Mar. 18, 2020.
Supplemental European Search Report from European Application No. 02729222.6 dated Aug. 20, 2009.
Response from European Application No. 02729222.6 dated Nov. 17, 2009.
Office Action from European Application No. 0279222.6 dated Sep. 23, 2010.
Response from European Application No. 02729222.6 dated Jan. 28, 2011.
Office Action from European Application No. 02729222.6 dated Sep. 7, 2011.
Response from European Application No. 02729222.6 dated Jan. 10, 2012.
Search Report from European Application No. 05757183.8 dated Oct. 4, 2012.
Office Action from European Application No. 05757183.8 dated Feb. 11, 2013.
Response from European Application No. 05757183.8 dated Aug. 19, 2013.
Search Report from European Application No. 05755966.8 dated Jun. 5, 2012.
Office Action from European Application No. 05755966.8 dated Sep. 27, 2012.
Response from European Application No. 05755966.8 dated Apr. 5, 2013.
Communication Pursuant to Article 94(3) EPC from European Application No. 05755966.8 dated Oct. 22, 2018.
Search Report from European Application No. 06112733.8 dated Jan. 12, 2007.
Response from European Application No. 06112733.8 dated Jan. 7, 2009.

(56) References Cited

OTHER PUBLICATIONS

Office Action from European Application No. 06112733.8 dated Feb. 19, 2009.
Search Report from European Application No. 12162767.3 dated Dec. 23, 2015.
Extended Search Report from European Application No. 14841802.3 dated Jan. 30, 2017.
Office Action from Japanese Application No. 2007-511105 dated Sep. 3, 2009.
Response from Japanese Application No. 2007-511105 dated Mar. 5, 2010 along with English translation of claims and relevant portion of remarks made in Amendment.
Office Action from Japanese Application No. 2007-515282 dated Jan. 7, 2011.
Response from Japanese Application No. 2007-515282 dated Apr. 7, 2011 along with English translation of claims and relevant portion of remarks made in Amendment.
Office Action from Japanese Application No. 2007-515282 dated Jul. 27, 2011.
Response from Japanese Application No. 2007-515282 dated Mar. 5, 2012 along with relevant portion of remarks made in Amendment.
Office Action from Japanese Application No. 2009-548397 dated Sep. 28, 2012.
Response from Japanese Application No. 2009-548397 dated Mar. 28, 2013 along with English translation of claims and relevant portion of remarks made in Amendment.
Office Action from Japanese Application No. 2010-511374 dated Dec. 28, 2012.
Response from Japanese Application No. 2010-511374 dated Jul. 5, 2013 along with English translation of claims and relevant portion of remarks made in Amendment.
English Translation of Office Action from Japanese Patent Application No. 2016-0540331 dated May 29, 2018.
Cook Medical brochure pages, Esophageal/Gastric Colonic: Snares, 3 pgs., date is at least as early as Jul. 1, 2013.
Juan-Marie et al. Double-Lumen Snare Injector: Introducing the Double-Lumen Concept in Ancillary Pollypectomy Equipment, Gastrointestinal Endoscopy, vol. 57, No. 5, 2003.
MTW Endoskopie, brochure, one page, date is at least as early as Jul. 1, 2013.
Olympus, EndoTherapy, Polypectomy, brochure, 3 pgs., date is at least as early as Jul. 1, 2013.
Extended Search Report from European Application No. 20152855.1 dated Jun. 16, 2020.
Office Action from U.S. Appl. No. 16/856,550 dated May 23, 2022.
Office Action from U.S. Appl. No. 16/846,581 dated Jul. 22, 2022.
English Translation of Office Action from Japanese Patent Application No. 2019-536289 dated Jun. 8, 2022.
English Translation of Office Action from Japanese Application No. 2019-536305 dated Jun. 8, 2022.
English translation of Office Action in Japanese Application No. 2014-004359 dated Jan. 20, 2015.
Extended European Search Report in European Application No. 08756773.1 dated Feb. 23, 2015.
Office Action from U.S. Appl. No. 14/565,024 dated Dec. 9, 2015.
Office Action from European Application No. 05757183.8 dated Nov. 16, 2015.
Response to Office Action from European Application No. 05757183.8 dated Mar. 17, 2016.
Extended European Search Report in European Application No. 08714094.3 dated Jan. 27, 2016.
Extended Search Report from European Application No. 18167984.6 dated Jul. 30, 2018.
Communication Pursuant to Article 94(3) from European Application No. 18167984.6 dated Jun. 6, 2019.

* cited by examiner

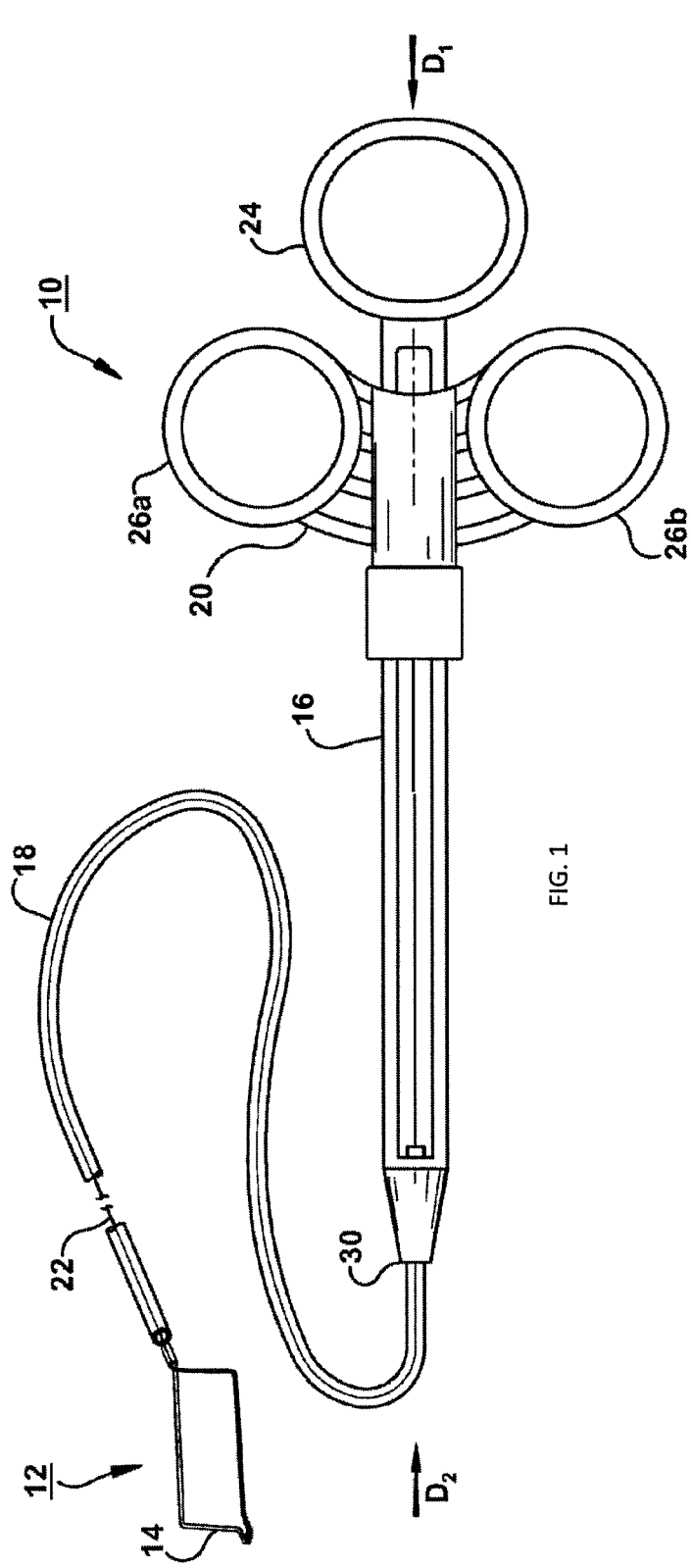
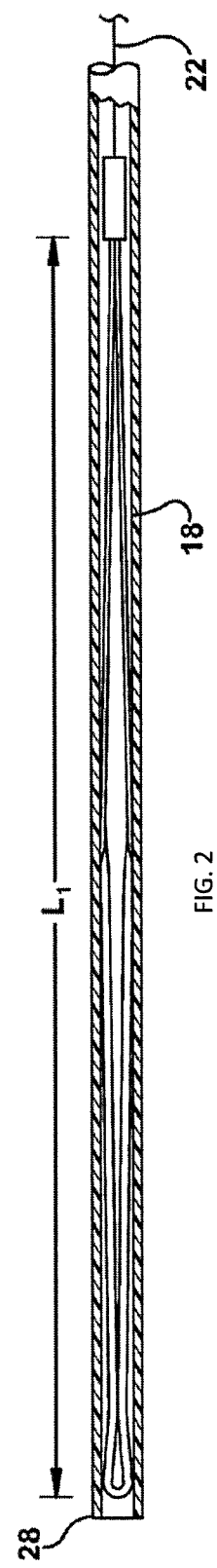

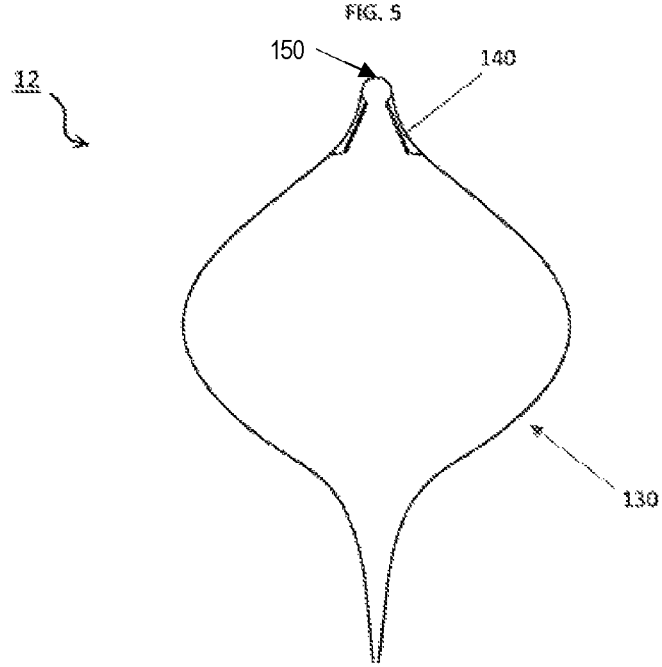
FIG. 6a AMENDED
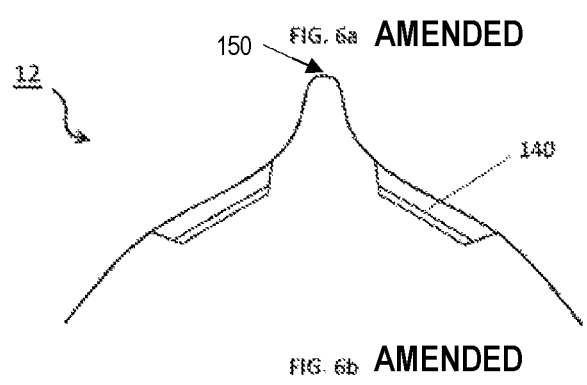
FIG. 6b AMENDED

ENDOSCOPIC SNARE DEVICE

CROSS-REFERENCES

This application is a continuation of U.S. patent application Ser. No. 15/866,401, filed Jan. 9, 2018, which claims the benefit of U.S. Provisional Patent Application No. 62/444,144, filed on Jan. 9, 2017, both disclosures of which are hereby incorporated herein by reference in their entirety.

TECHNICAL FIELD

The present subject matter relates generally to endoscopic snare devices.

BACKGROUND

Polypectomy, or the removal of polyps, has become one of the most common endoscopic procedures in gastrointestinal endoscopy today. Its relative simplicity often belies the effectiveness of the procedure at preventing colorectal cancer. The National Polyp Study (NPS) demonstrated a reduction in the incidence of colorectal cancer of 76%-90% following colonoscopic polypectomy. Standard practice for polypectomy has been to use an electrocautery or "hot" snare to remove polyps due to the fact that it reduces the risk of bleeding as a result of the coagulation effect created by the current. Electrocautery, however, can create inadvertent damage to healthy tissue and may not be necessary for smaller sized polyps where bleeding risk is not a concern.

A "cold" snare, such as US Endoscopy Group Inc.'s Exacto® snare, is designed for polypectomy procedures where diminutive polyps are encountered. It enables a clean cut that reduces polyp "fly away" form the resection site. Studies comparing Exacto® snare to hot snares have shown that, for diminutive polyps in the 3-8 mm range, there is no difference in postpolypectomy bleeding and it requires less time to use than hot snares while being just as safe and effective.

SUMMARY

The present subject matter describes a tissue removal tool for use with an endoscope. The tool comprises a loop formed by a piece of wire and movable between an open position and a closed position, and a transmitting assembly comprising: a handle; and a link having a first end attached to the handle and a second end attached to the loop, the loop portion being movable between the open and closed position by action of the handle. The loop is defined in the open position by a proximal portion and a distal portion. The widest portion of the loop is more proximal to a proximal end of the loop than the mid-point of the length of the loop is.

The present subject matter further describes a tissue removal tool having a cutting section disposed along the distal portion of the loop.

BRIEF DESCRIPTION OF THE DRAWINGS

The features and advantages of the general inventive concepts will become apparent from the following detailed description made with reference to the accompanying drawings.

FIG. 1 is a perspective view of a retrieval device, showing a snare in an open position;

FIG. 2 is an enlarged sectional view of a portion of the retrieval device of FIG. 1, showing the snare in a closed position within a conduit;

FIGS. 6a-6b show a second embodiment of the loop with microtomes or cutting elements;

DETAILED DESCRIPTION OF INVENTION

Figure 3:
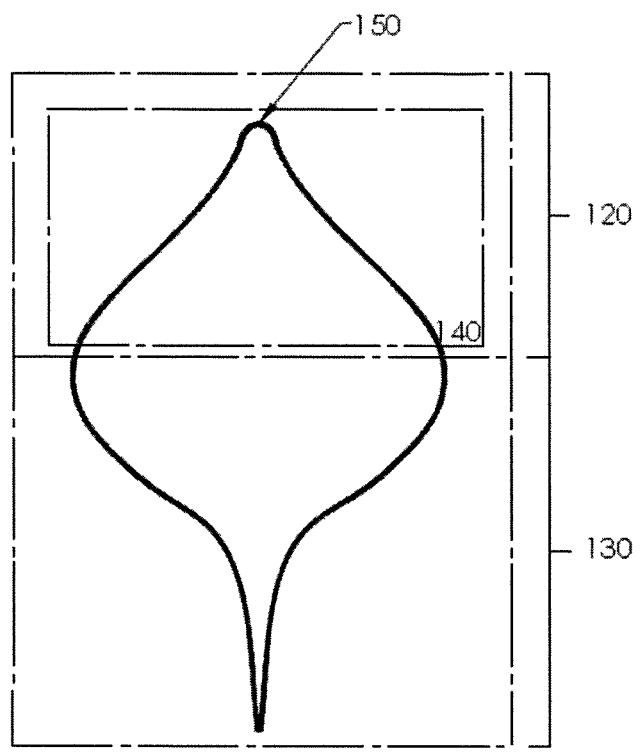
FIG. 3 is an embodiment of the loop with a general cable form design.

This Detailed Description merely describes exemplary embodiments in accordance with the general inventive concepts and is not intended to limit the scope of the invention or the claims in any way. Indeed, the invention as described by the claims is broader than and unlimited by the exemplary embodiments set forth herein, and the terms used in the claims have their full ordinary meaning.

The general inventive concepts will now be described with occasional reference to the exemplary embodiments of the invention. This general inventive concept may, however, be embodied in different forms and should not be construed as limited to the embodiments set forth herein. Rather, these embodiments are provided so that this disclosure will be thorough and complete, and will fully convey the scope of the general inventive concepts to those skilled in the art.

Unless otherwise defined, all technical and scientific terms used herein have the same meaning as commonly understood by one of ordinary skill in the art encompassing the general inventive concepts. The terminology set forth in this detailed description is for describing particular embodiments only and is not intended to be limiting of the general inventive concepts. As used in this detailed description and the appended claims, the singular forms "a," "an," and "the" are intended to include the plural forms as well, unless the context clearly indicates otherwise.

Unless otherwise indicated, all numbers such as, for example, numbers expressing measurements or physical characteristics, used in the specification and claims are to be understood as being modified in all instances by the term "about." Accordingly, unless otherwise indicated, the numerical properties set forth in the specification and claims are approximations that may vary depending on the suitable properties sought to be obtained in embodiments of the invention. Notwithstanding that the numerical ranges and parameters setting forth the broad scope of the general inventive concepts are approximations, the numerical values set forth in the specific examples are reported as precisely as possible. Any numerical values, however, inherently contain certain errors necessarily resulting from error found in their respective measurements.

The present application describes a tissue removal tool for use with an endoscope, comprising: a loop formed by a piece of wire and movable between an open position and a closed position; a handle; and a link having a first end attached to the handle and a second end attached to the loop, the loop being movable between the open and closed position by action of the handle, wherein the loop is defined in the open position by a proximal portion and a distal portion.

Referring to FIG. 1, the exemplary tool 10 includes a loop 12 formed by a piece of wire 14. A wire of any suitable material may be used to form the loop, such as for example, a metal, such as stainless steel, nitinol, plastic or carbon nanotube, glass fiber, or hybrid technology. The loop may also be formed by a monofilament or a cable. The variations in the wire shape and orientation along the length of the wire may be made by mechanically bending or twisting a preformed wire into the desired shape and orientation, or the wire may be originally manufactured to have the desired shape and orientation, such as for example, a preformed plastic piece. A suitable material will be flexible and have memory to allow deployment and retrieval of the loop. The wire forms a plurality of segments separated by collapse-resistant bends to define a loop opening. The loop is movable between an open position, or deployed position, and a closed position, or retrieved position. The loop 12 is illustrated in an open position in FIG. 1. The loop is polygon-shaped and, specifically, the loop is generally diamond-shaped. In FIG. 2, the loop 12 is shown in a closed position within a distal portion of the tool 10. As discussed herein, the loop 12 is within a conduit 18. In this closed or retrieved position, the exemplary loop has a length $L_1$.

The tool may include a support assembly and a transmitting system for moving the loop between an open position and a closed position. In the exemplary tool 10 illustrated in FIG. 1, the support assembly includes a base or body 16 and an elongated hollow tube, tubular member or conduit 18. The transmitting assembly includes a handle 20 movable relative to the body 16 and a link 22. One end of the link is fixed to the handle and a second end is remote from the body. As shown in FIGS. 1 and 2, the link 22 extends substantially through a length of the conduit 18. The conduit 18 may be any suitable, small-diameter tube formed of a low-friction flexible material such as, for example, polytetrafluoroethylene, high density polyethylene, polyether block amide, or other comparable materials. The conduit 18 defines a lumen with an opening at a distal second end 28, as best seen in FIG. 2 which shows a cross-sectional view of a distal portion of the tool 10. A proximal first end 30 of the conduit is fixed to the body 16.

The handle allows an operator to move the loop back and forth between a deployed position, as shown in FIG. 1, and a closed position, as shown in FIG. 2. Referring again to FIG. 1, the body 16 includes a fixed ring 24 at a proximal end. The handle 20 may be slid by an operator relative to the body 16 by use of the handle 20 and, specifically, by use of one or both of two rings 26a, 26b. The handle 20 is mounted over an elongated section of the body 16 and is movable relative to the body in the direction $D_1$ to deploy the loop 12, or in an opposing direction $D_2$ to close the loop 12. For example, an operator may place a finger in each of the rings 26a, 26b and a thumb of the same hand in the body ring 24. By moving the two fingers in the direction $D_1$, an operator can move the handle 20 relative to the body 16. This movement of the handle will deploy the loop. In contrast, the handle 20 can be slid in the opposite direction $D_2$ by pulling one's fingers towards one's thumb to close the loop.

A link 22 is connected to the handle 20 for transferring axial motion from the handle 20 to other parts of the device. The link may be constructed of any suitable rigid material, and may be solid, hollow, or any suitable elongated object or combination of objects. The link may be one piece or formed from a series of pieces and connections, such as for example, hypodermic tubes, swage connections, and cables. The link 22 has a first end fixed to the handle 20 and a second end remote from the body 16. As shown in the drawings, the link extends substantially through the conduit 18.

Figure 4:
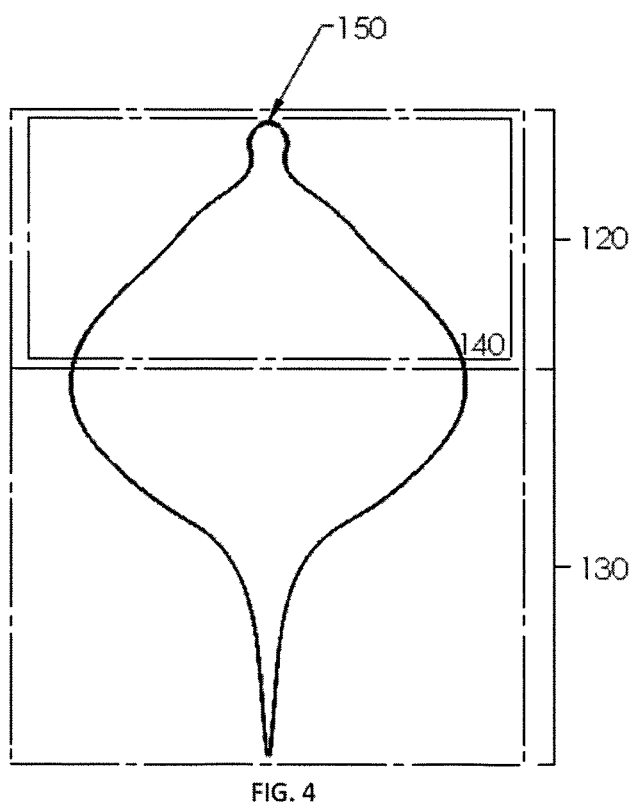
FIG. 4 is an embodiment of the loop with a general monofilament form design.

FIG. 3 shows a general form for a cable cold cutting snare loop. FIG. 4 shows a general form for a monofilament cold cutting snare loop. The loops 12 comprise a distal portion 120 and a proximal portion 130. The loop comprises a cutting section 140 along the distal portion 120 of the loop 12. The cutting section 140 covers roughly ⅓ to ½ of the loop 12, and may be continuous or discrete. In some embodiments, the cutting section 140 extends about 1-5 mm out from the distal end 150 in either direction. In some embodiments, the cutting section 140 extends about 5 mm to 15 mm out from the distal end 150 in either direction. In some embodiments, the cutting section 140 extends about 10 mm out from the distal end 150 in both directions. In some embodiments, the cutting section 140 extends about 5 mm to 15 mm out from the distal end 150 in both directions. The cutting section 140 needs to be thin enough to provide cutting pressure to tissue. The cutting section 140 comprises a diameter of 0.36 mm or thinner so as to enable cold cutting of tissue. In some embodiments, the diameter is 0.30 or thinner. The cutting mostly occurs on the distal portion 120 of the snare by virtue of tensile mechanics of the snare as it is retracted into the tubular member 18. The distal tip 150 may also be optimized to dissipate stress uniformly so as not to deform during retraction.

The proximal portion 130 of the loop 12 generally does not perform cutting but provides assistance and support to encircle and recruit tissue for cutting. Increasing the stiffness of the proximal portion allows for greater indentation of the tissue which improves tissue recruitment. The stiffer proximal portion 130 can be about the proximal ⅓ to ½ of the loop 12. The proximal portion may vary in stiffness along its length.

Figure 5:
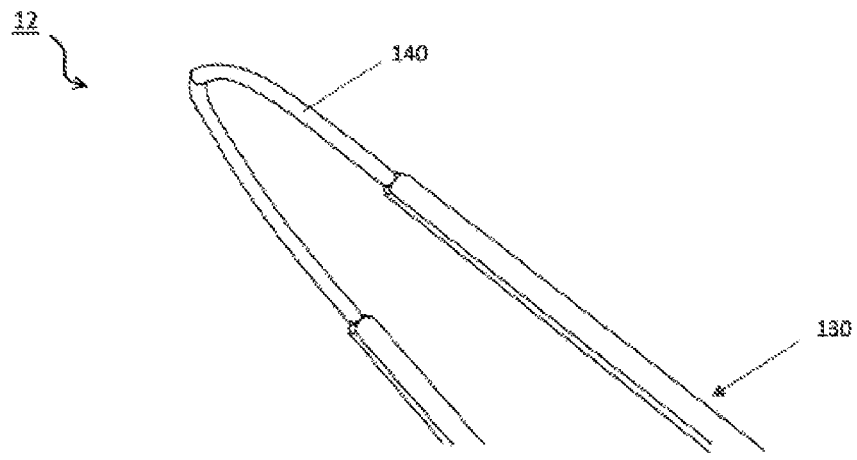
FIG. 5 is a first embodiment of the loop with a distal cutting section and a proximal portion formed from separate wires.

In an embodiment shown as FIG. 5, the proximal portion 130 comprises flat wire or coined cable. The cutting section 140 generally comprises thinner wire than the proximal portion 130. These separate portions may be joined together by welding, gluing, crimping, swaging, soldering, or other techniques familiar to those skilled in the art.

In an embodiment shown as FIGS. 6a and 6b, the cutting section 140 comprises cutting blades disposed on an otherwise non-cutting snare wire.

Figure 7:
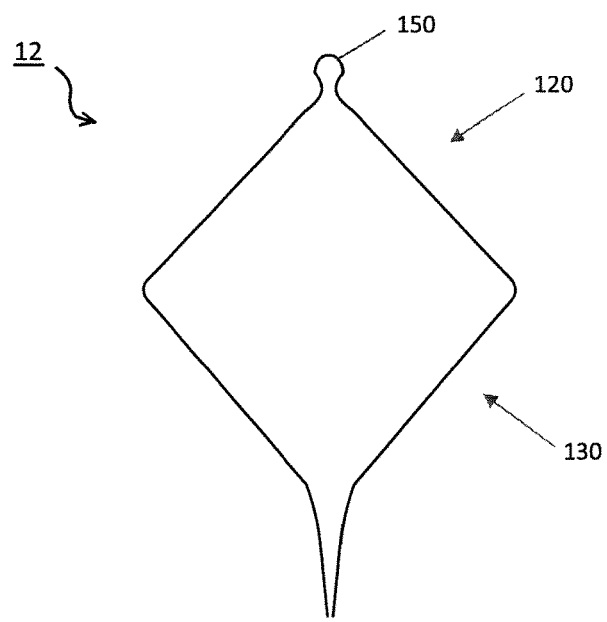
FIG. 7 is a third embodiment of the loop with a torsion tip.

In an embodiment shown as FIG. 7, the loop 12 is a solid rectangular wire filament loop with a torsion tip 150 to preserve its shape.

Figures 8A, 8B, 8C:
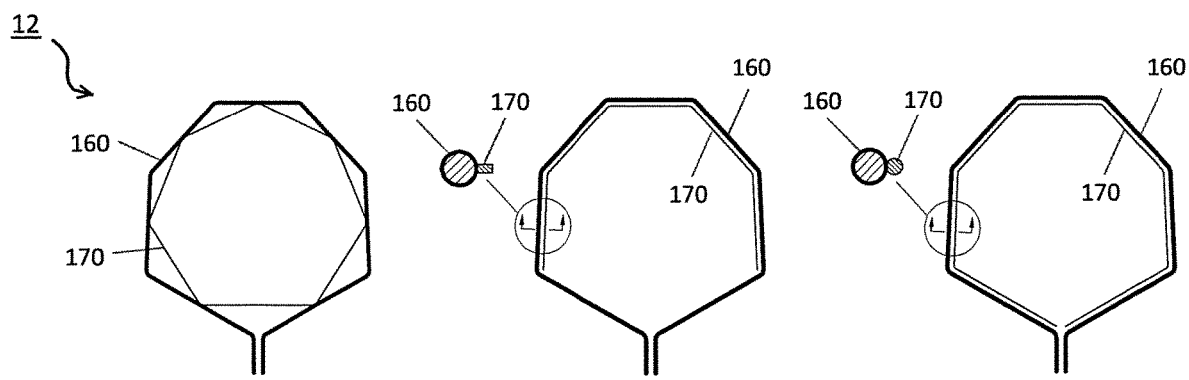
FIGS. 8a-8c show a fourth embodiment of the loop with separate loop elements.

In some embodiments, such as those shown as FIGS. 8a-8c, the loop 12 comprises an inner loop 170 (i.e., cutting section) and an outer loop 160. The inner loop 170 is bonded (i.e., welded or other known suitable bonding methods) to the outside loop 160 in at least one location. The inner loop 170 comprises a thinner wire that is configured to be more effective for cold cutting. The outer loop 160 is thicker and stiffer than the inner loop 170. The outer loop 160 allows the loop 12 to indent and recruit tissue. In some embodiments, the inner loop 170 only covers the distal/mid portion of the loop 12, since that is where the cutting truly occurs. In some embodiments, the inner loop 170 is a full loop, since this may make fixturing/manufacture more efficient. In some embodiments, the inner loop 170 has a round cross-section. In some embodiments, the inner loop 170 is a flat or square wire.

Figure 9A:
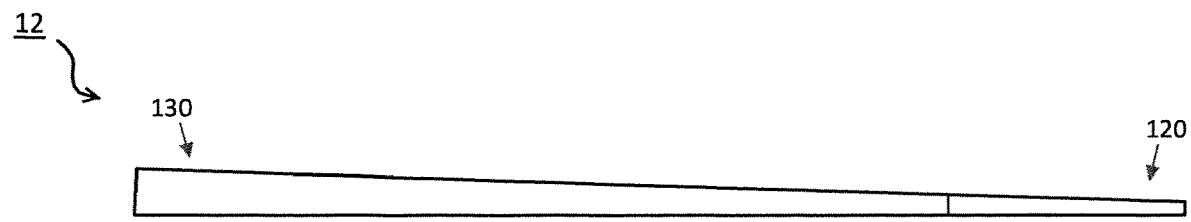
FIGS. 9a-9b show a fifth embodiment of the loop with a tapered or ground portion.
Figure 9B:
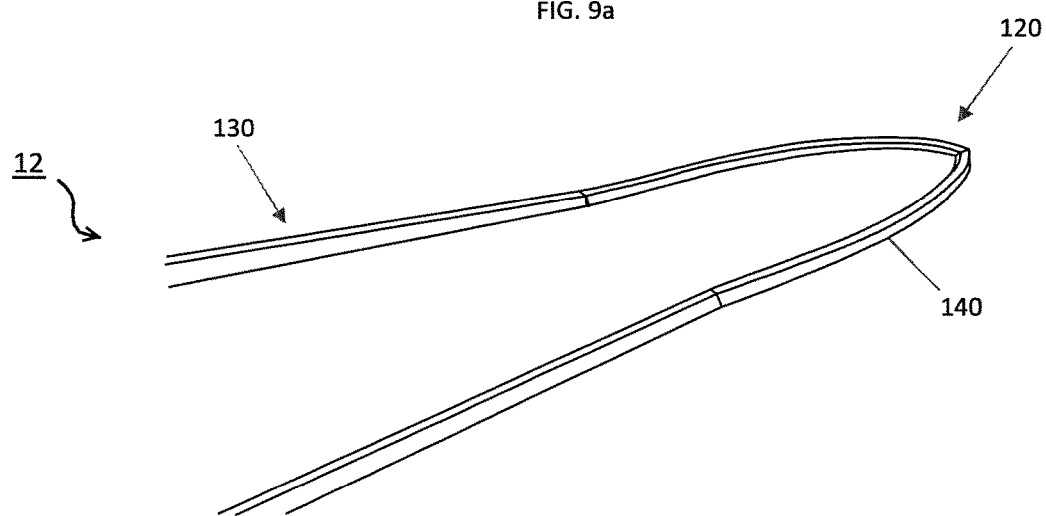

In an embodiment shown in FIGS. 9a and 9b, the loop 12 comprises tapered or ground wire. The proximal portion 130 is thicker than the distal portion 120. The tool may further comprise mechanisms for promoting positioning of the loop 12 within the body, such as a rotatable link 22. In some embodiments, the link 22 is of sufficiently less torsional rigidity than the legs of the loop 12.

Figure 10:
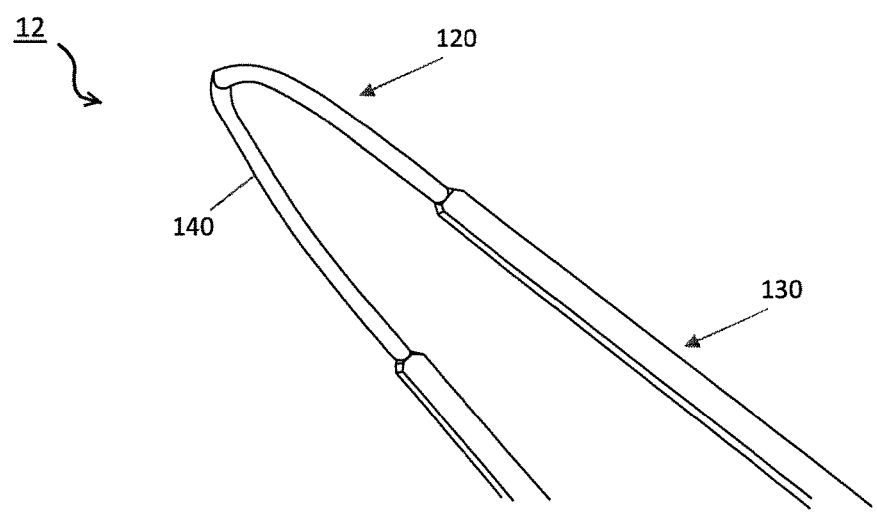
FIG. 10 is a sixth embodiment of the loop with a coined proximal portion.

In an embodiment shown in FIG. 10, the loop 12 comprises cable or monofilament loop with a coined proximal portion 130 and non-coined distal portion 120.

Figure 11:
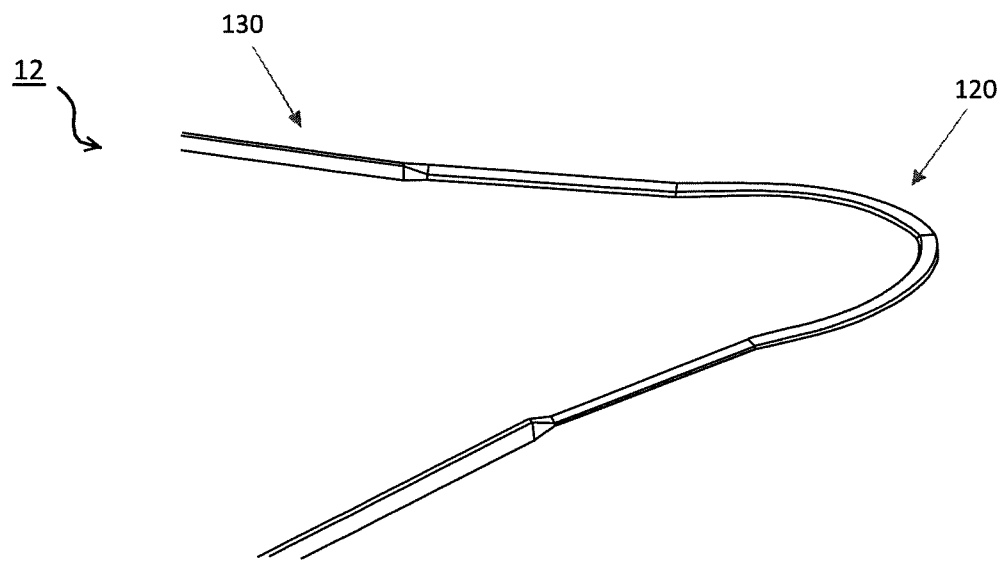
FIG. 11 is a seventh embodiment of the loop with a coined or non-coined proximal portion and a coined distal portion.

In an embodiment shown in FIG. 11, the loop 12 comprises a cable or monofilament loop with a coined distal portion 120, which creates a sharp inner edge to provide for cutting action. In some embodiments, the proximal portion may also be coined in a perpendicular plane to the distal coined portion.

Figure 12A:
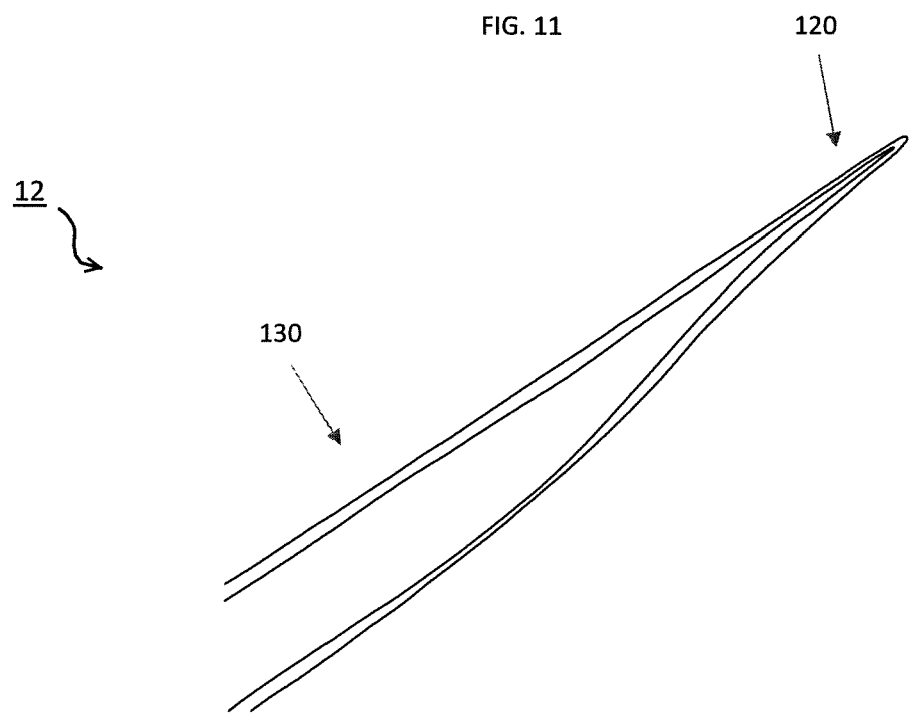
FIGS. 12a-12b show an eighth embodiment of the loop with a plurality of coined sections.
Figure 12B:
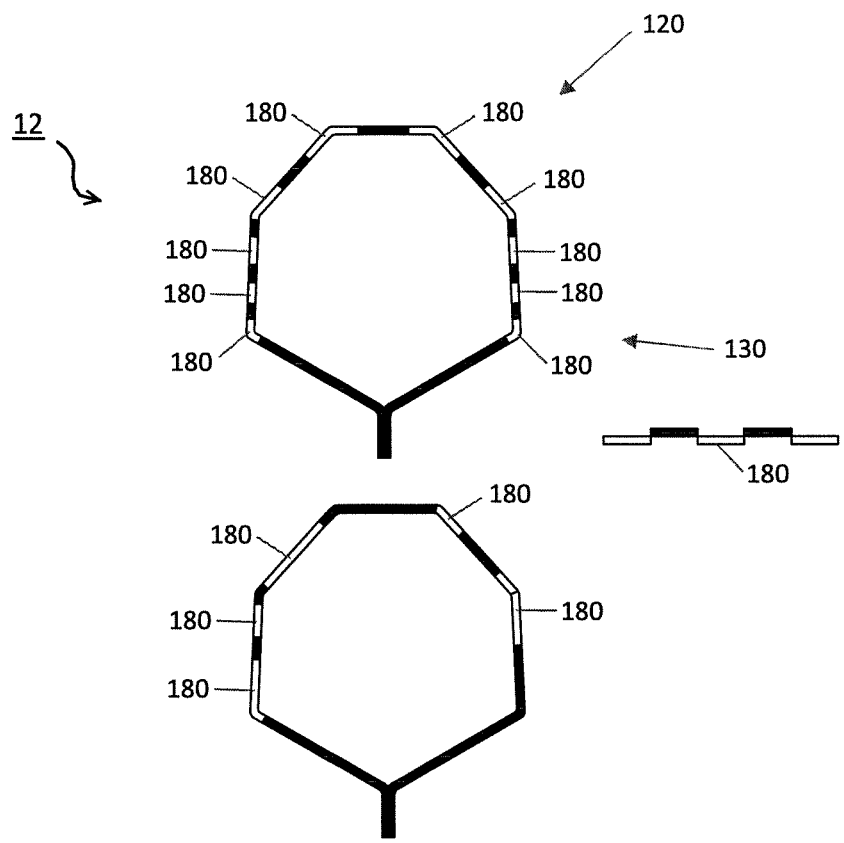

In some embodiments shown in FIGS. 12a and 12b, the loop 12 comprises coined at various locations 180 so as to be advantageous for cutting or grasping tissue. It may be several small level and cross-sectional changes, a few longer sections and may be either symmetrical or asymmetrical with respect to the loop centerlines (vertical and horizontal).

Figure 13:
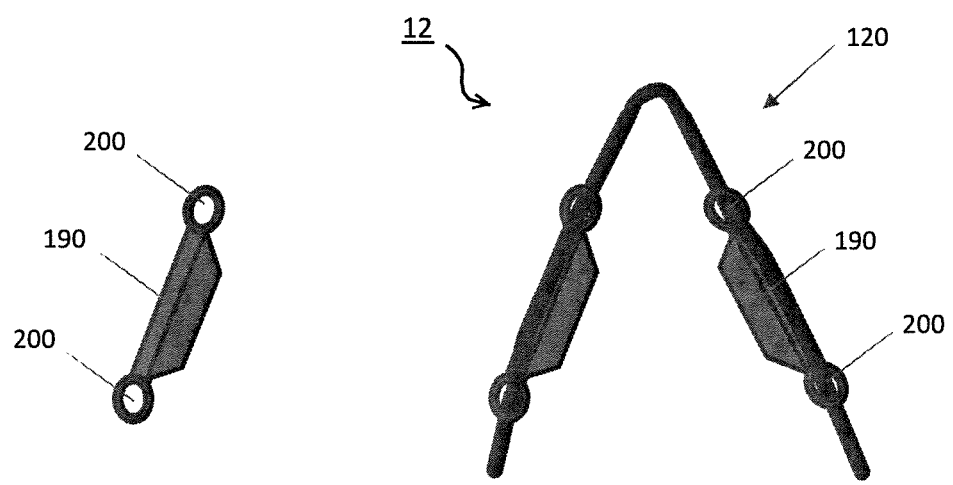
FIG. 13 is a ninth embodiment of the loop showing a method for mounting cutting elements.

In an embodiment shown in FIG. 13, the cutting section comprises a cutting element 190 with eyelets 200. The eyelets 200 could have the wire slid through and then crimped, welded, glued or otherwise bonded in place. The eyelets 200 could be any opening shape, such as round or square.

Referring now to FIG. 4, in the exemplary loop 12, the wire is bent at the distal tip 150 to form a torsion tip, or a nearly 360° circular tip. The tip allows for dissipation of stress through the snare, something that is of particular importance when cold snaring because of the relatively larger forces used compared to hot snaring. One feature to help to facilitate this is to use multifilament cable. The strands in the cable move relative to one another and allow for stresses to be more evenly spread across the snare body. To achieve the same effect in monofilament wire, one can create a loop that mimics a standard torsion spring without increasing the cutting thickness of the tip. Because the tip is a loop and not a simple bend, stress is distributed more evenly around the entire circumference upon closing, minimizing plastic deformation.

The distal tip 150 of the tool may have alternative shapes. US 2014/0052142 A1 and US2015/0066045 A1 disclose multiple distal loop or coil tip designs, the contents of which are incorporated herein. The wire may form a torsion tip with a 180° bend. In another distal tip, the wire within the 180° bend may be in a landscape orientation. In another exemplary distal tip, the loop is formed by a wire having two portions. The two wire portions form an atraumatic tip at a distal most point. As assembled, the wire portions function as a loop in the same way as discussed herein.

Figure 14:
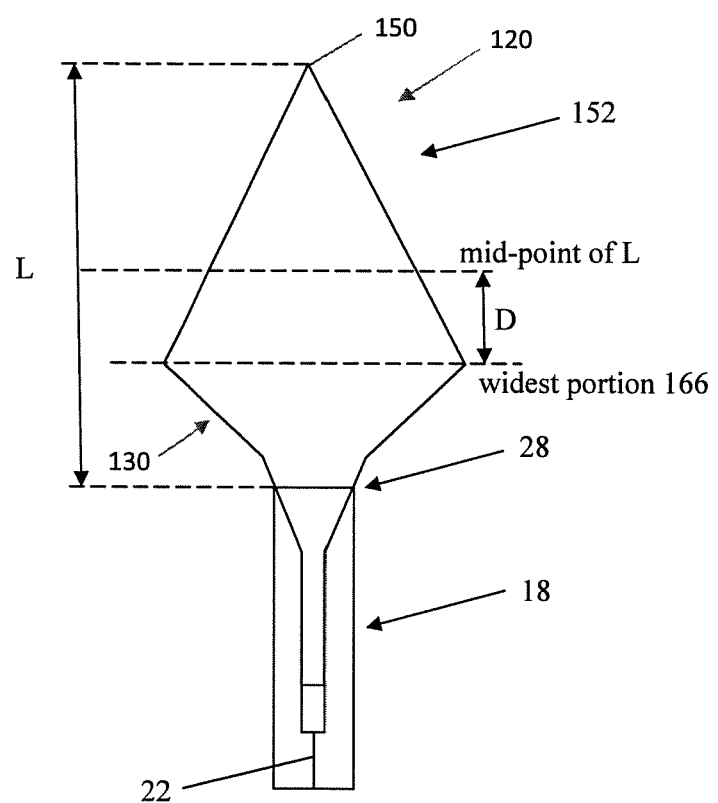
FIG. 14 is another embodiment of the loop detailing the loop.

Another aspect of the present subject matter is to provide a new shape of the loop. Referring to FIG. 14, in some embodiments, the loop 152 comprises a widest portion 166 and a length L measured between a proximal end and a distal end. The proximal end is defined where the loop begins to close during retraction into the tubular member, irrespective of where the loop connection physically may occur. The distal end is defined by the most distal end, or ends, of the loop 152. In any instance where there are proximal legs that are excessively long, and/or the distal tip is inverted or of any other unusual geometry, the midpoint shall be considered only with respect to the broad portions of the form, which is defined between the proximal end and the distal end(s). The widest portion 166 of the loop 152 is more proximal to the tubular member 18 than the mid-point of the length L of the loop 152 is. In other words, the widest portion 166 is closer to the tubular member 18 than the mid-point of the length L of the loop 152, such that the loop 152 is easier to be controlled during the procedures. In some embodiments, the distance D from the mid-point of the length L of the loop 152 to the widest portion 166 of the loop 152 is about 3%-45% of the length L. In some embodiments, the distance D from the mid-point of the length L of the loop 152 to the widest portion 166 of the loop 152 is about 10%-35% of the length L. In some embodiments, the distance D from the mid-point of the length L of the loop 152 to the widest portion 166 of the loop 152 is about 12%-25% of the length L.

It should be understood that some or all of the features described above may be applied to any suitable endoscopic devices or combination of endoscopic devices, such as snare-needle device, a multistage snare, or an endoscopic retrieval device.

A person skilled in the art should understand that although the above-described snare features are designed for cold cutting, they may also be utilized with electrocautery without compromising the features that make them useful for gathering and cutting tissue.

A person skilled in the art should understand that the endoscopic device described in the present subject matter is not necessary to comprise the support assembly (including the base and the elongated tubular member) and/or the transmitting assembly (including the handle and the link). A handle may be formed by or connected to the proximal end of the loop.

While various inventive aspects, concepts and features of the general inventive concepts are described and illustrated herein in the context of various exemplary embodiments, these various aspects, concepts and features may be used in many alternative embodiments, either individually or in various combinations and sub-combinations thereof. Unless expressly excluded herein all such combinations and sub-combinations are intended to be within the scope of the general inventive concepts. Still further, while various alternative embodiments as to the various aspects, concepts and features of the inventions (such as alternative materials, structures, configurations, methods, circuits, devices and components, alternatives as to form, fit and function, and so on) may be described herein, such descriptions are not intended to be a complete or exhaustive list of available alternative embodiments, whether presently known or later developed. Those skilled in the art may readily adopt one or more of the inventive aspects, concepts or features into additional embodiments and uses within the scope of the general inventive concepts even if such embodiments are not expressly disclosed herein. Additionally, even though some features, concepts or aspects of the inventions may be described herein as being a preferred arrangement or method, such description is not intended to suggest that such feature is required or necessary unless expressly so stated. Still further, exemplary or representative values and ranges may be included to assist in understanding the present disclosure; however, such values and ranges are not to be construed in a limiting sense and are intended to be critical values or ranges only if so expressly stated. Moreover, while various aspects, features and concepts may be expressly identified herein as being inventive or forming part of an invention, such identification is not intended to be exclusive, but rather there may be inventive aspects, concepts and features that are fully described herein without being expressly identified as such or as part of a specific invention. Descriptions of exemplary methods or processes are not limited to inclusion of all steps as being required in all cases, nor is the order that the steps are presented to be construed as required or necessary unless expressly so stated.

We claim:

1. A tissue removal tool for use with an endoscope, comprising:
    a loop formed by a piece of wire and movable between an open position and a closed position, wherein the loop is defined in the open position by a proximal portion and a distal portion, and wherein portions of the loop are coined;
    a cutting section disposed at least at the distal portion of the loop, wherein the cutting section comprises thinner wire than the proximal portion of the loop;
    a transmitting assembly comprising:
        a handle; and
        a link having a first end attached to the handle and a second end attached to the loop, the loop portion being movable between the open and closed position by action of the handle.

2. The tissue removal tool of claim 1, wherein both the distal portion and the proximal portion of the loop are coined.

3. The tissue removal tool of claim 2, wherein the proximal portion of the loop is coined in a perpendicular plane to the distal coined portion.

4. The tissue removal tool of claim 1, wherein the wire is bent at a distal end of the distal portion to form a torsion tip.

5. The tissue removal tool of claim 1, wherein the loop is a monofilament loop.

6. The tissue removal tool of claim 1, wherein a widest portion of the loop is more proximal to a proximal end of the loop than a mid-point of the length of the loop is.

7. The tissue removal tool of claim 6, wherein a distance from a mid-point of the length of the loop to the widest portion of the loop is about 3%-45% of the length.

8. The tissue removal tool of claim 7, wherein a distance from the mid-point of the length of the loop to the widest portion of the loop is about 10%-35% of the length.

9. The tissue removal tool of claim 8, wherein the distance from the mid-point of the length of the loop to the widest portion of the loop is about 12%-25% of the length.

10. The tissue removal tool of claim 1 further comprising: a support assembly comprising a base and an elongated tubular member, wherein the handle is movable relative to the base, and the link extends through at least a portion of the tubular member.

11. The tissue removal tool of claim 1, wherein the cutting section covers about ⅓ to ½ of the loop at the distal portion of the loop.

12. The tissue removal tool of claim 1, wherein the cutting section extends about 5 mm to 15 mm from a distal end of the loop in either direction.

13. The tissue removal tool of claim 12, wherein the cutting section extends about 10 mm from a distal end of the loop in either direction.

14. The tissue removal tool of claim 1, wherein the cutting section comprises a diameter of 0.36 mm or thinner.

15. The tissue removal tool of claim 1, wherein the coined portions of the loop are either symmetrical or asymmetrical with respect to the loop centerlines.

16. A tissue removal tool for use with an endoscope, comprising:
    a loop formed by a piece of wire and movable between an open position and a closed position, wherein the loop is defined in the open position by a proximal portion and a distal portion, and wherein portions of the loop are coined;
    a cutting section disposed at least at the distal portion of the loop, wherein the cutting section comprises thinner wire than the proximal portion of the loop;
    a transmitting assembly comprising:
        a handle; and
        a link having a first end attached to the handle and a second end attached to the loop, the loop portion being movable between the open and closed position by action of the handle; and
    wherein the cutting section is a cutting element comprising cutting blades disposed on an otherwise non-cutting snare wire.

17. The tissue removal tool of claim 16 further comprising: a support assembly comprising a base and an elongated tubular member, wherein the handle is movable relative to the base, and the link extends through at least a portion of the tubular member.

18. The tissue removal tool of claim 16, wherein both the distal portion and the proximal portion of the loop are coined.

19. The tissue removal tool of claim 16, wherein the proximal portion of the loop is coined in a perpendicular plane to the distal coined portion.

20. The tissue removal tool of claim 16, wherein the wire is bent at a distal end of the distal portion to form a torsion tip.

21. The tissue removal tool of claim 16, wherein the loop is a monofilament loop.

22. The tissue removal tool of claim 16, wherein the cutting section covers about ⅓ to ½ of the loop at the distal portion of the loop.

23. The tissue removal tool of claim 16, wherein the cutting section extends about 5 mm to 15 mm from a distal end of the loop in either direction.

24. The tissue removal tool of claim 23, wherein the cutting section extends about 10 mm from a distal end of the loop in either direction.

25. The tissue removal tool of claim 16, wherein the cutting section comprises a diameter of 0.36 mm or thinner.

26. The tissue removal tool of claim 16, wherein the coined portions of the loop are either symmetrical or asymmetrical with respect to the loop centerlines.

27. A tissue removal tool for use with an endoscope, comprising:
    a loop formed by a piece of wire and movable between an open position and a closed position, wherein the loop is defined in the open position by a proximal portion and a distal portion, and wherein portions of the loop are coined;
    a cutting section disposed at least at the distal portion of the loop, wherein the cutting section comprises thinner wire than the proximal portion of the loop;
    a transmitting assembly comprising:
        a handle; and
        a link having a first end attached to the handle and a second end attached to the loop, the loop portion being movable between the open and closed position by action of the handle; and wherein the loop comprises an inner loop and an outer loop, wherein the inner loop is secured to the outer loop in at least one location, and the inner loop is thinner than the outer loop.

28. The tissue removal tool of claim 27, wherein the inner loop only covers the distal portion of the loop.

29. The tissue removal tool of claim 27, wherein the inner loop substantially covers the whole loop.

30. The tissue removal tool of claim 27 further comprising: a support assembly comprising a base and an elongated tubular member, wherein the handle is movable relative to the base, and the link extends through at least a portion of the tubular member.

31. The tissue removal tool of claim 27, wherein both the distal portion and the proximal portion of the loop are coined.

32. The tissue removal tool of claim 27, wherein the proximal portion of the loop is coined in a perpendicular plane to the distal coined portion.

33. The tissue removal tool of claim 27, wherein the wire is bent at a distal end of the distal portion to form a torsion tip.

34. The tissue removal tool of claim 27, wherein the loop is a monofilament loop.

35. The tissue removal tool of claim 27, wherein the cutting section covers about $\frac{1}{3}$ to $\frac{1}{2}$ of the loop at the distal portion of the loop.

36. The tissue removal tool of claim 27, wherein the cutting section extends about 5 mm to 15 mm from a distal end of the loop in either direction.

37. The tissue removal tool of claim 36, wherein the cutting section extends about 10 mm from a distal end of the loop in either direction.

38. The tissue removal tool of claim 27, wherein the cutting section comprises a diameter of 0.36 mm or thinner.

39. The tissue removal tool of claim 27, wherein the coined portions of the loop are either symmetrical or asymmetrical with respect to the loop centerlines.

* * * * *